US011298472B2

(12) United States Patent
Sadeghinia et al.

(10) Patent No.: US 11,298,472 B2
(45) Date of Patent: Apr. 12, 2022

(54) ULTRASONIC NEBULIZER

(71) Applicant: SOSD Health & Medical Innovations Inc., Winnipeg (CA)

(72) Inventors: Ali Sadeghinia, Karaj (IR); Ali Darbandi, Tehran (IR); Abbas Ostadalipour, Tehran (IR); Armin Sahba, Sari (IR); Nasser Ashgriz, Thornhill (CA)

( * ) Notice: Subject to any disclaimer, the term of this patent is extended or adjusted under 35 U.S.C. 154(b) by 0 days.

(21) Appl. No.: 17/234,492

(22) Filed: Apr. 19, 2021

(65) Prior Publication Data

US 2021/0330899 A1 Oct. 28, 2021

Related U.S. Application Data

(60) Provisional application No. 63/014,772, filed on Apr. 24, 2020.

(51) Int. Cl.
*A61M 11/00* (2006.01)
*A61M 15/00* (2006.01)

(52) U.S. Cl.
CPC ......... *A61M 11/005* (2013.01); *A61M 11/001* (2014.02); *A61M 15/0021* (2014.02); *A61M 2205/8206* (2013.01)

(58) Field of Classification Search
CPC .............. A61M 11/001; A61M 11/005; A61M 15/0021; A61M 2205/8206; A61M 15/0085; B41J 2/025
See application file for complete search history.

(56) References Cited

U.S. PATENT DOCUMENTS

| | | | | |
|---|---|---|---|---|
| 3,812,854 | A * | 5/1974 | Michaels | A61M 11/005 128/200.16 |
| 4,912,357 | A * | 3/1990 | Drews | B05B 17/0623 310/323.01 |
| 5,950,619 | A * | 9/1999 | van der Linden | B05B 17/0607 128/200.16 |
| 6,196,218 | B1 * | 3/2001 | Voges | B05B 17/0607 128/200.14 |
| 6,730,066 | B1 * | 5/2004 | Bennwik | A61M 11/00 222/94 |
| 8,899,230 | B2 * | 12/2014 | Immel | A61M 15/0098 128/203.15 |
| 9,339,838 | B2 * | 5/2016 | Moran | A61M 11/005 |
| 10,195,633 | B2 * | 2/2019 | Crichton | B05B 17/0646 |

(Continued)

*Primary Examiner* — Justine R Yu
*Assistant Examiner* — Matthew D Ziegler
(74) *Attorney, Agent, or Firm* — Nasser Ashgriz; UIPatent Inc.

(57) ABSTRACT

An ultrasonic nebulizer is provided that has a liquid chamber to receive a liquid. A piezoceramic transducer is attached to one end of the liquid chamber. The piezoceramic has an orifice to allow the liquid inside the chamber to exit. A plunger movably and sealbly is inserted into the liquid chamber from its other end, which is moved by a moving mechanism to push the liquid out of the liquid chamber. The plunger forms a small liquid droplet on the surface of the piezoceramic. Oscillation of the piezoceramic at megahertz frequencies results in atomization and formation of small droplets from the surface of the sessile droplet. The present nebulizer is a total consumption nebulizer, since all its droplets are substantially within 2 to 5 microns, which is the size range to penetrate into the lunges of a user.

15 Claims, 5 Drawing Sheets

(56) References Cited

U.S. PATENT DOCUMENTS

| | | | | |
|---|---|---|---|---|
| 10,583,038 B2* | 3/2020 | Ivri | ........................ | A61F 9/0008 |
| 10,888,117 B2* | 1/2021 | Danek | ................... | A61M 11/005 |
| 2010/0083956 A1* | 4/2010 | Fukumoto | ................... | B41J 2/14 |
| | | | | 128/200.14 |
| 2013/0079732 A1* | 3/2013 | Burt | .................... | B05B 17/0607 |
| | | | | 604/290 |
| 2013/0299607 A1* | 11/2013 | Wilkerson | ........... | B05B 17/0676 |
| | | | | 239/328 |
| 2016/0058960 A1* | 3/2016 | Papania | ............ | A61M 15/0063 |
| | | | | 600/103 |
| 2018/0289907 A1* | 10/2018 | Marmur | ................. | A24F 40/05 |

* cited by examiner

ULTRASONIC NEBULIZER

RELATED APPLICATION

The present invention claims the priority date of the provisional patent application No. 63/014,772 filed on Apr. 24, 2020.

FIELD OF THE INVENTION

This invention relates to nebulizers and in particular to nebulizers to be used as inhaler for providing a precise dose of medicine.

BACKGROUND OF THE INVENTION

Respiratory disease affects a significant portion of the population globally. Asthma and COPD alone affect over 480 m patients. Asthma is a chronic lung disease that inflames and narrows the airways. Asthma causes recurring periods of wheezing (a whistling sound when you breathe), chest tightness, shortness of breath, and coughing. About 230 m people have asthma and the disease is common among children. More than 380,000 asthma deaths per year globally. Untreated asthma limits the ability to live an active life, still many asthmatics do not have the level of control over their asthma as they could have. A contributing factor is improper drug delivery to the patient's lungs. Asthma is normally treated by inhaling long-term control medicine (controller) and quick-relief medicines (reliever) or a combination of both medication (combination medication) from asthma inhalers.

The inhaled route remains crucial for the treatment of bronchial diseases. However, drug deposition and subsequent treatment effectiveness are highly dependent on inhalation technique, which is incorrect in many patients with asthma and COPD. Many inhalation devices are available and others are currently being developed with the aim of simplifying required handling, and thus improving treatment safety. Nonetheless, at present, proper training and regular checking of inhalation technique remain critical to optimise treatment effectiveness.

Nebulizers used for the delivery of pharmaceutical compounds are widely known and they are used for the delivery of several types of medicines treating lung disease and as well as for systemic delivery. Several types of inhalers are known, from those comprising a dosing valve and a pressurized canister invented to nebulizers and powder-based inhalers.

From the device perspective, the variables that need to be optimized to emit an accurate and consistent dose with the inhaler are: the volume of the drug solution that is loaded in the device (taking into account its "dead volume"); the viscosity of the drug solution; the air flow and pressure in case of jet nebulizers; and the tubing, mask, or mouthpiece used.

The currently available nebulizers generate a wide range of droplet sizes, usually between 1-30 microns. However, only 2 to 5 micron size droplets can penetrate deep into the lungs for an effective drug delivery. Droplets larger than 5 microns are collected in the mouth and upper respiratory tree, which results in more than 80% loss of the drug. Large particles or droplets deposit by impaction in the upper respiratory tree of the lung (oropharyngeal and tracheobronchial region), where air velocity is high and the air flow is turbulent. However, particles in the size range of 0.5-5 µm deposit by sedimentation in the terminal bronchioles and alveolar regions. In general, aerosol particles should be between 2-5 microns and as close as possible to monodispersity to increase deposition at the desired site of action, and increase the efficacy of the treatment. Medicines of higher cost than inexpensive water and physiologic saline solutions are often used in nebulizers. Accordingly, arranging it so that every drop of the medicine is used once the nebulizer has been filled is important in terms of economy.

One type of inhalers are the nebulizers, which can be in the form of jet nebulizer or ultrasonic nebulizer, that differ in the force used to generate the aerosol from the respective liquid. Depending on the model and the manufacturer, nebulizers generate 1-30 µm droplets, however, larger droplets are either separated or are deposited in the upper tract. Nebulizers do not require patient coordination between inhalation and actuation; thus they are useful for pediatric, elderly, ventilated, non-conscious patients, or those who are unable to use pMDIs or DPIs. Nebulizers have the capability of delivering larger doses compared to the other aerosol devices even though this will require longer administration times. Jet nebulizers are based on Venturi's principle which states that fluid pressure decreases as its passes through a narrow sectional area. In ultrasonic nebulizers, sound waves are created due to the vibration of piezoelectric crystals at high frequency, creating crests that break the liquid into small droplets. The piezoceramics convert an electrical signal to a mechanical vibration.

The prior art disclosing ultrasonic atomizer use a mesh plate having tapered minute holes which flare from one side of the plate toward the other. The mesh plate is arranged in such a manner that the side in which the minute holes have the openings of larger diameter opposes the upper end face of the pump shaft of an ultrasonic pump, and such that a minute gap is produced between the mesh plate and the upper end face of the pump shaft. The number of minute holes formed in the mesh plate has a direct influence upon the amount of atomization. The greater the number of minute holes per unit surface area, the greater the amount of atomization. When the number of minute holes is increased, however, there is a decline in the strength of the mesh plate itself. There is a need for some expedient which can provide strength while allowing an increase in the number of minute holes.

SUMMARY OF THE INVENTION

The present invention provides a total consumption nebulizer. A novel total consumption nebulizer based on ultrasonic nebulization technology is disclosed, which can generate an aerosol that all of its droplets are within 2 to 5 microns. Therefore, when this nebulizer is used as an nebulizer, almost all of the drug is used by the user without any waste, thus it is referred to as a total consumption nebulizer. In addition, this allows the user to know the exact amount of drug dosage, as well as reducing patient's drug expenses.

The present ultrasonic nebulizer generates 2-5 micron droplets without using a mesh technology. It used a new method of introducing a nano-volume of a liquid on the surface of a piezoceramic that is oscillating at megahertz frequencies. Since there is no mesh, there is no corrosion issue. This nebulizer requires low power to the piezo, since there is no mesh. A flat piezo with an orifice at its center is used, and the liquid is fed through the orifice from its bottom surface. An extra pump is needed to pump the liquid through a small orifice.

One novelty of the device is on the method of introduction of the liquid onto the piezoelectric surface. A small volume of liquid of less than 100 nanoliter of a pharmacological solution is introduced onto a piezoelectric transducer operating at about 3 MHz frequency. Another novelty of our nebulizer is on how to generate such small nanoliter volumes on the surface of the piezo in a continuous and on demand conditions. A Mega Hertz frequency piezo transducer with a small orifice at its center is used to cause ultrasonic atomization of the fluid. A pharmaceutical fluid is forced through the small orifice using a syringe pump. Therefore, a micro syringe pump is designed as part of this nebulizer. As soon as the liquid reaches the surface of the piezo, it will atomize into small droplets of 2-5 microns. The piezo orifice size, the piezo frequency and voltage, as well as the liquid flow rate are so designed to generate small droplets.

The advantages of the present nebulizer over all of the prior art nebulizers are that the present nebulizer generates droplets in the range of 2-5 microns, it has a more uniform droplet size distribution, the amount of drug used by the patient is precisely quantifiable, the drug usage by the patient does not dependent on breath capacity, the drug delivery is targeted and local, the aerosol generated has low momentum, but high concentration, the drug delivery is highly efficient at smaller doses, the drug dispensing is quick at high volumes, and nebulizer is compact and portable.

One object of the present invention is to provide a better nebulizer to improve patient's lives and provide a high quality respiratory devices.

Another object of the present invention is to provide an nebulizer that can generate droplets which are all within 2-5 microns.

Another object of the present invention is to provide an ultrasonic atomizer that can pump the liquid through a syringe pump through a small orifice. Other features and advantages of the present invention will be apparent in the description of an embodiment given with reference to the drawings.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION OF PREFERRED EMBODIMENTS

An ultrasonic nebulizer according to the present invention comprises a piezoceramic transducer with Mega Hertz resonance frequency. The system operates based on injecting a nanoliter volume of a liquid on the surface of the piezoceramic, and operating the piezoceramic at MHz frequencies. Different embodiments of this nebulizer are developed to achieve this goal.

Figure 1:
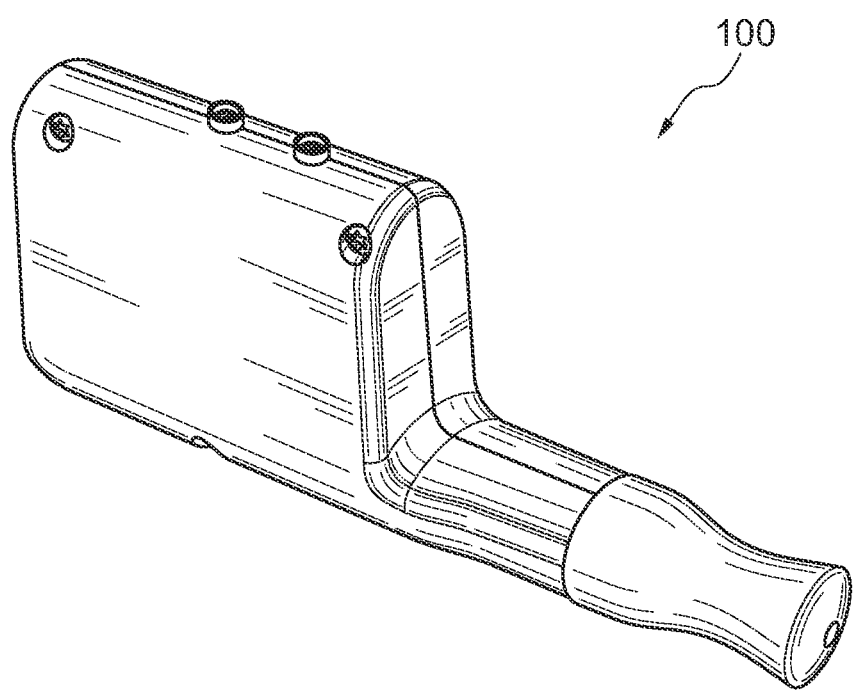
FIG. 1 is a perspective view of the first embodiment of the present ultrasonic nebulizer.
Figure 2:
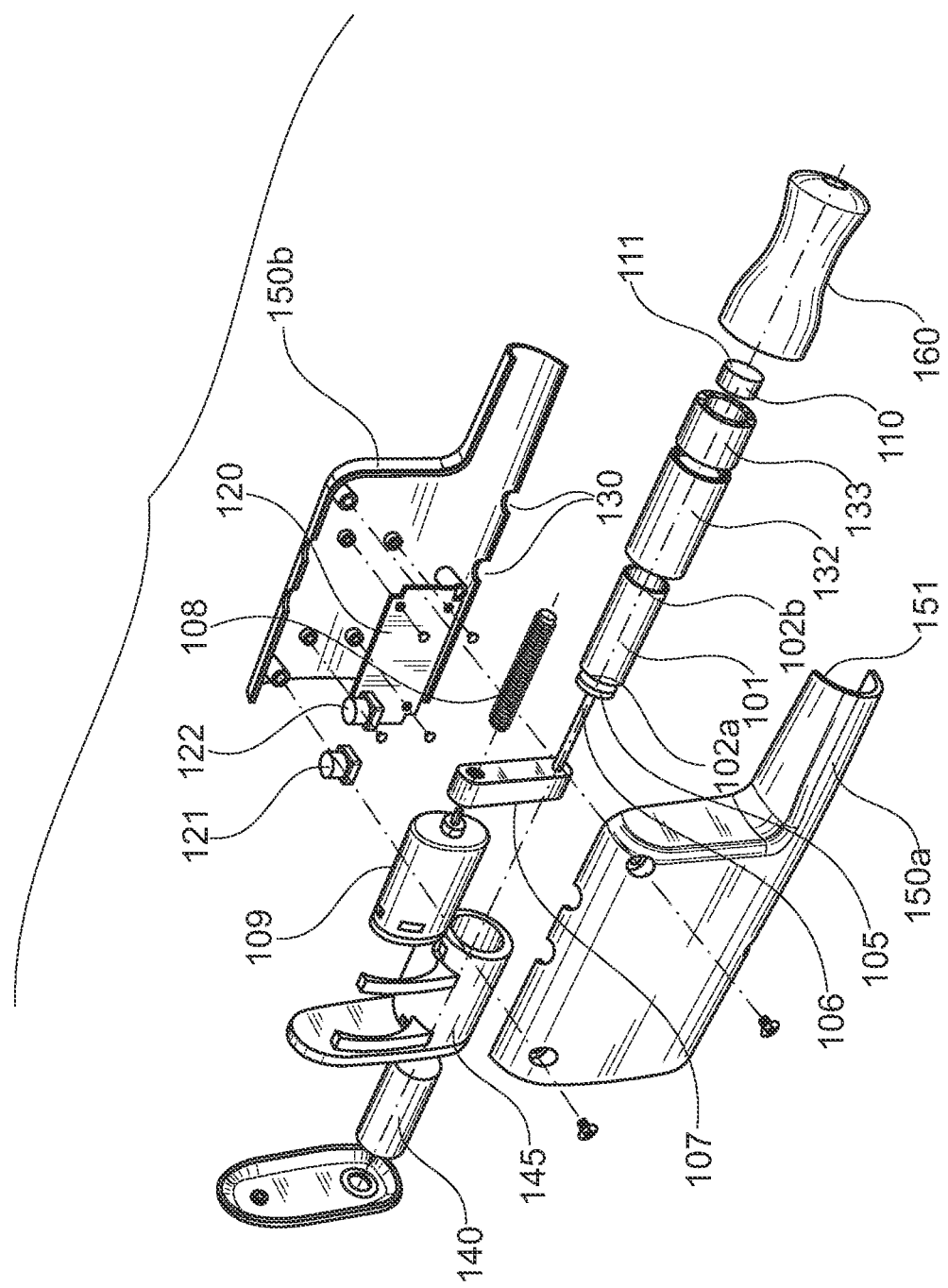
FIG. 2 is an exploded view of the present nebulizer.

FIG. 1 shows a perspective of the present nebulizer 100 and FIG. 2 is an exploded view of the nebulizer showing its main elements. The main elements of the present nebulizer comprise of the followings. A liquid container 101 to be filled by a liquid drug. The liquid container is a cylindrical tube with a proximal end 102a and a distal end 102b. The liquid container may have a sensor to indicate the volume of the liquid inside the chamber. A piezoceramic transducer 110 that has an orifice 111 at its center, is fixed to the distal end 102b of the liquid container 101. The piezoceramic is substantially the same diameter of the liquid container tube 101. However, other designs can be made in which the piezoceramic is different size, and even much larger than the container diameter. The diameter of the orifice is small enough, preferably in the range of 300 microns to 1 mm. The small size of the orifice is important to provide a small sessile droplet on the surface of the piezoceramic, and also to prevent liquid leakage out of the chamber without an external pressure. The proximal end of the container 102a has a movable plunger 105 which is sealably inserted into the liquid container. The plunger 105 cannot be removed from the container and it can only attach and detach to a moving rod 106. A forward movement of the moving rod 106 pushes the plunger inward, forcing the fluid inside the container through the orifice.

Figure 3:
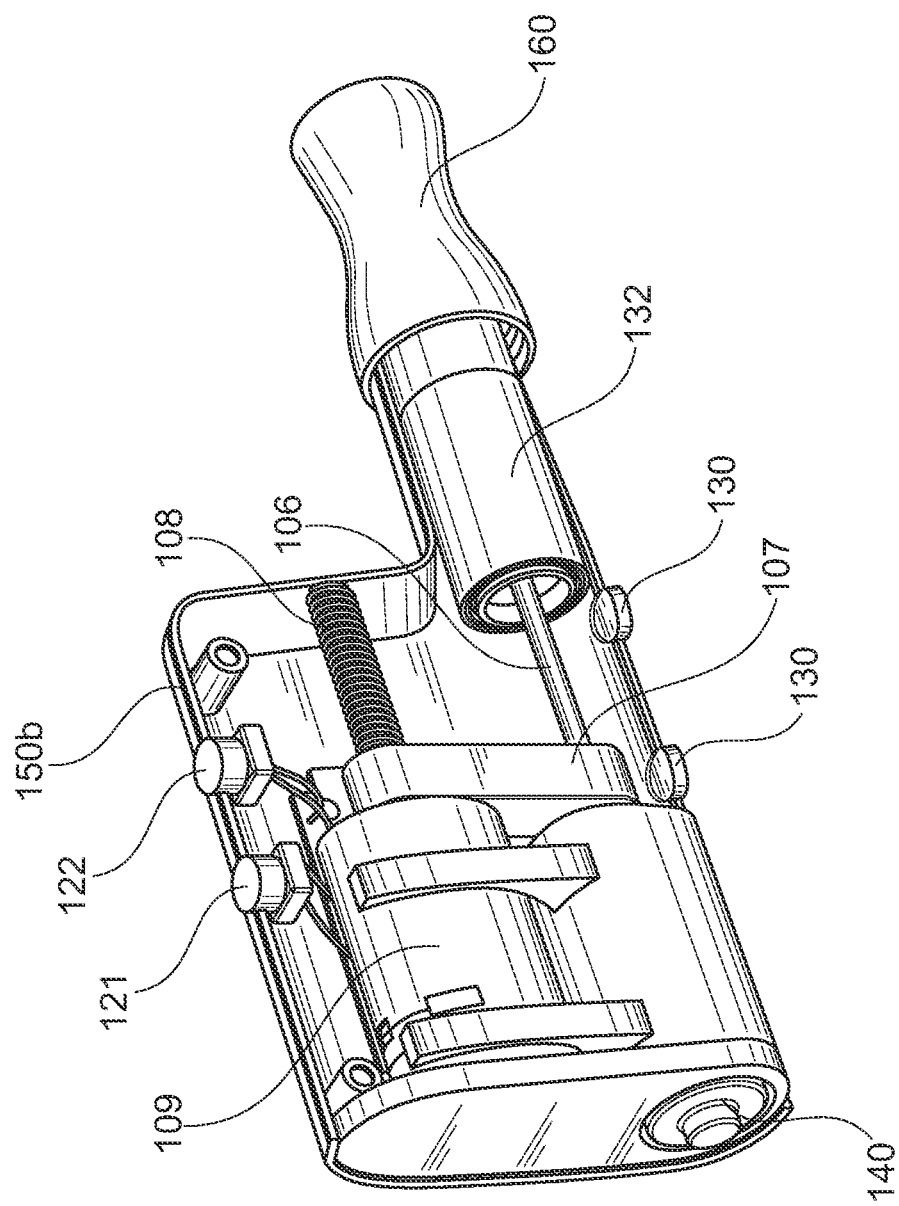
FIG. 3 is a view of the present nebulizer with its front cover off.
Figure 4:
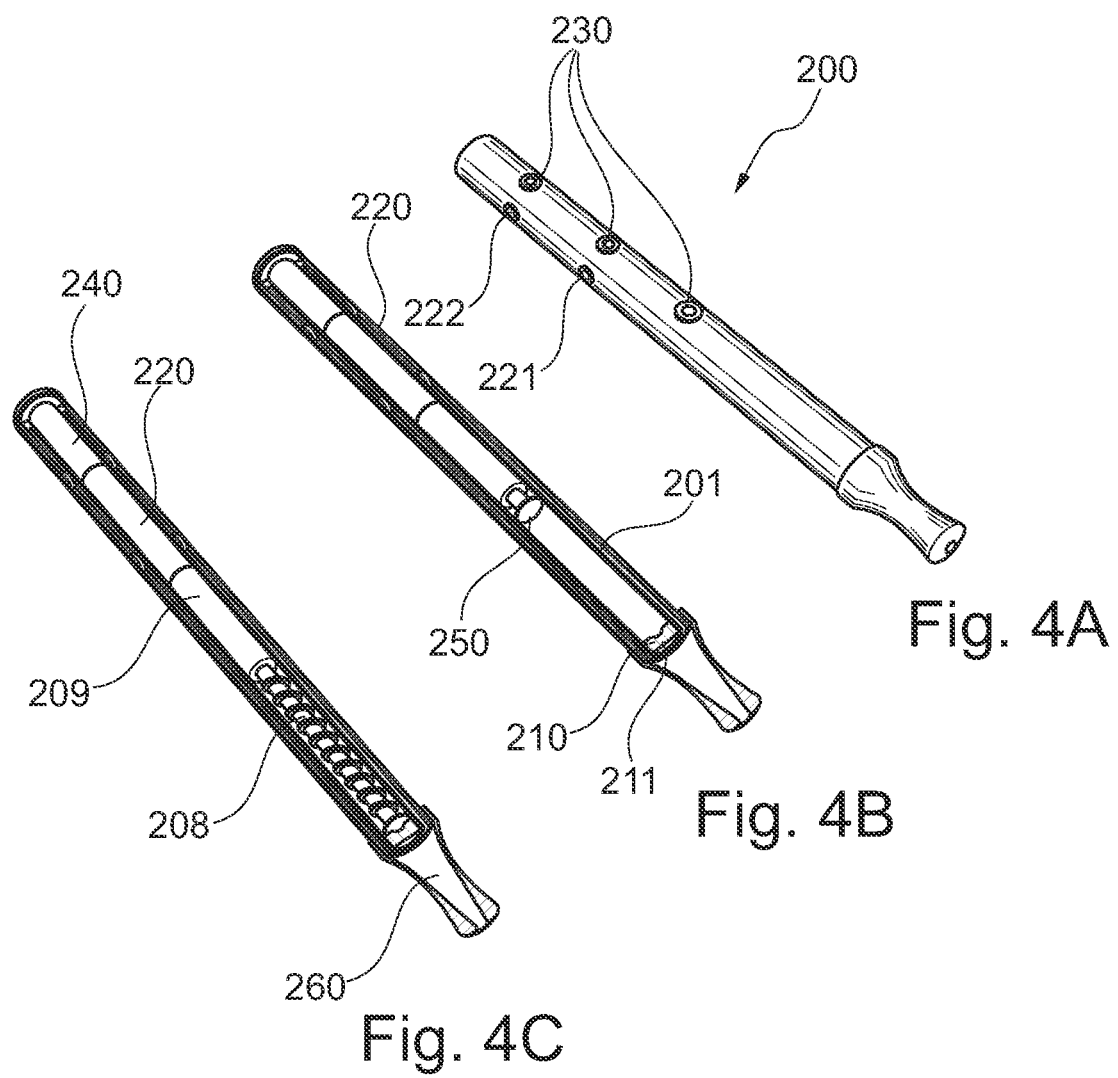
FIG. 4A is a perspective view of the second embodiment of the present nebulizer.
FIG. 4B is a perspective view of the second embodiment of the present nebulizer with its front cover taken off and the plunger at its un-extended position.
FIG. 4C is a perspective view of the second embodiment of the present nebulizer with its front cover taken off and the plunger at its extended position.
Figure 5:
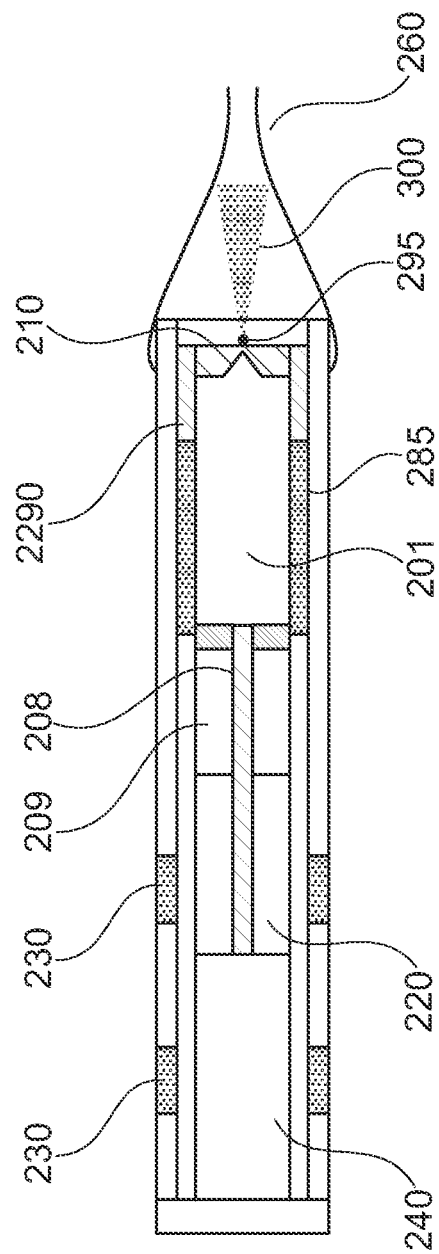
FIG. 5 is a schematic of the second embodiment of the present nebulizer showing different parts of the nebulizer.

A preferred mechanism for the forward movement of the plunger is shown in FIGS. 2 and 3. The moving rod 106 is attached to a connecting rod 107, which is connected to a screw shaft 108 of a motor 109. As can be seen in FIG. 3, the rotation of the motor, rotates the screw shaft, which causes the connecting rod to move forward or backward depending on the direction of the movement of the motor. The movement of the connecting rod moves the moving rod, which moves the plunger.

The forward movement of the plunger pushed the fluid inside the container towards the orifice of the piezoceramic, forming a small nanoliter liquid volume on the surface of the piezo. It is crucial to move the fluid slowly so that the liquid does not jet out of the orifice and it only accumulates on the surface of the piezoceramic. The sessile droplet has to be small enough to allow proper atomization of the liquid without generating large droplets. The sessile droplets between 1 to 100 nanoliter in volume or about 300 to 500 microns in diameter have shown to generate 2-5 micron droplets and no large droplets.

A control unit 120 causes the piezoceramic to oscillate at MHz frequencies, controls the operation of the motor and switches. The piezoceramic can be operated at different nominal frequencies, such as 1-10 MHz. The control unit has the circuitry that generate the proper frequency and power to run a predefined piezoceramic, for example, a piezoceramic at 3 MHz frequency and at 20 volts. Different size piezoceramics may provide optimum oscillation at different frequency and powers. Therefore, the nebulizer has to be tuned for the piezoceramic that is used. Also, more viscous fluids may require higher voltages to atomize. Therefore, the power to the piezo may be changed to atomize a particular fluid. The controller allows a user to change the frequency and the power to the piezoceramic. The control system can operate the nebulizer in different conditions, including running the piezo and the plunger only when the ON button is pushed, or dispense a predetermined amount of liquid volume at each push of the ON button.

A battery 140 powers the whole system, including the piezoceramic and the motor. Preferably a rechargeable battery that is charged with an input jack from an external AC adapter or the like is used. The battery is provided at a cavity in the lower portion of the housing. In another embodiment of the present nebulizer, the nebulizer has a rechargeable battery with a charging case, so that once the nebulizer is put inside the case, it is automatically charged. This makes sure that the nebulizer is always ready for use. Other charging devices, such as crank charging attachment to allow the user to charge the nebulizer even when there is no eclectic outlet can be used as well.

A mouth piece 160 connected to the distal end of the nebulizer allows the user to inhale the aerosol generated by the piezoceramic oscillation. Any variety of mouth piece can be used with this nebulizer. In order to refill the container, the mount piece and the front part of the nebulizer are removed and the liquid container is filled with a liquid drug.

In the preferred design, the nebulizer housing is made of two sections, 105a and 105b, which are configured to hold the piezoceramic, the electronic circuit, the power source, and control system. The two sections are screwed to each other for a sturdy device. Other designs and configuration can be considered to provide the main elements of the present nebulizer. Air can enter the nebulizer 100 through several air inlets 130. The air then goes through a cylindrical filter 132 that is the placed in the channel 151 that is formed in the nebulizer shells 150a and 150b. The air filer goes around the fluid container 101.

Preferably an air swirler 133 is also used to swirl the air that exits the channel. The air swirler helps in dispersion of the droplets of the aerosol and therefore reduces the potential for collision and coalescence of the droplets and thereby keeps the droplet sizes small. The swirling air also keeps the aerosol droplets at the center of the flow, and prevent the droplets from colliding with the walls of the mouth piece.

The controller is turned on and off with and ON/OFF switch 121. The system is preferably designed for single button operation. By pushing an ON button, the piezo is turned on, and the syringe pump is pushed forward, forcing the liquid through the orifice of the piezo, generating the aerosol. As soon as the liquid reaches the surface of the piezo, it will atomize into small droplets between 2-5 microns. In operation, a user draws air from the mouth piece, while pushing on the ON button. The controller can be programmed with a secondary switch 122 to provide pulses of aerosol for a predetermined period. The pulses are designed to disperse a predetermined amount of liquid aerosol.

The nebulizer 100 is compact and ergonomically designed to be easily carried by a patient. A silent, one-button operation enables its discreet use. This nebulizer can operate at any angle and there is no need to keep at any particular direction. This is another advantage of the present nebulizer as compared to many of the mesh ultrasonic nebulizers which need to be kept at a particular direction to keep the liquid in contact with the mesh.

FIG. 4A-C shows another embodiment of the present nebulizer. In this embodiment, the nebulizer is substantially cylinder with all the main elements in a cylinder alignment. FIG. 4A shows a perspective of the present nebulizer 200 and FIGS. 4B and 4C show the cut views of the nebulizer. A liquid container 201 to be filled by a liquid drug. The liquid container may be made of a transparent material to allow the user determine volume of the liquid inside the chamber. A piezoceramic transducer 210 that has an orifice 211 at its center, is fixed to the distal end of the liquid container 201. The piezoceramic is substantially the same diameter of the liquid container tube 201. A movable plunger 205 which is sealably inserted into the liquid container. The plunger 205 is connected to a screw shaft 208 of a motor 209. As can be seen in FIGS. 4A and 4B, the rotation of the motor, rotates the screw shaft, which moves the plunger. The forward movement of the plunger pushed the fluid inside the container towards the orifice of the piezoceramic, forming a small nanoliter liquid volume on the surface of the piezo. It is crucial to move the fluid slowly so that the liquid does not jet out of the orifice and it only accumulates on the surface of the piezoceramic. Alternatively, a linear motion motor or any similar mechanism can be used to move the plunger.

A control unit 220 causes the piezoceramic to oscillate at MHz frequencies, controls the operation of the motor and switches. A battery 240 powers the whole system, including the piezoceramic and the motor. Preferably a rechargeable battery that is charged with an input jack from an external AC adapter or the like is used. The battery is provided at a cavity in the lower portion of the housing. In another embodiment of the present nebulizer, the nebulizer has a rechargeable battery with a charging case, so that once the nebulizer is put inside the case, it is automatically charged. A mouth piece 260 connected to the distal end of the nebulizer allows the user to inhale the aerosol generated by the piezoceramic oscillation. Any variety of mouth piece can be used with this nebulizer. In order to refill the container, the mount piece and the front part of the nebulizer are removed and the liquid container is filled with a liquid drug. Air can enter the nebulizer 200 through several air inlets 230. The air then goes through the shell of the nebulizer to exits through the mouthpiece.

The controller 220 is turned on and off with and ON/OFF switch 221. The system is preferably designed for single button operation. By pushing an ON button, the piezo is turned on, and the syringe pump is pushed forward, forcing the liquid through the orifice of the piezo, generating the aerosol. As soon as the liquid reaches the surface of the piezo, it will atomize into small droplets between 2-5 microns. In operation, a user draws air from the mouth piece, while pushing on the ON button. The controller can be programmed with a secondary switch 222 to provide pulses of aerosol for a predetermined period. The pulses are designed to disperse a predetermined amount of liquid aerosol. FIG. 5 shows more details of the nebulizer of FIG. 4A (not to scale), which shows a sessile droplet 295 sitting on the outer surface of the piezoceramic transducer 210. The liquid in container 201 is forced by the screw shaft 208 of a motor 209, onto the piezo to have a small sessile droplet 295 formed on its surface. In operation, when the nebulizer is turned on, a user will use the mouth piece 260 to suck air in. Air will then enter through openings with air filters 230, flows through an internal air filter 285, and a swirler (a set of swirling vanes) 290, and then mixes with the aerosol 300 that is generated by the sessile droplet 295 to exit the mouth piece. The swirling vanes form an air vortex that keeps the aerosol at the central region of the flow and prevents their collision with the walls of the mouth piece.

Liquid Indicator: In another embodiment of the present invention, one part of the case that hold liquid and a part of the case in front of it is transparent. This allows the user to see the level of the liquid inside the nebulizer and refill the nebulizer if needed.

The present nebulizer can generate droplet sizes in the 1-5-μm range, ideal for effective pulmonary therapy. The present nebulizer has considerable advantages over other conventional nebulizers, and, in particular, ultrasonic atomization, in that it uses significantly less power, does not require a mesh plate.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A meshless ultrasonic nebulizer comprising:

a liquid chamber having a proximal end, a distal end, and a volume to receive a liquid having a set of properties;

a piezoceramic transducer having a planar top surface and a back surface and being operable in a range of 1-5 Mega Hertz frequency attached to the distal end of the liquid chamber, the piezoceramic transducer further consisting of an orifice at its center to allow for a liquid to enter from the liquid chamber into the orifice from the back surface and onto the top surface of the piezoceramic transducer to sustain a volume of a liquid on the top surface;

a plunger movably and sealably inserted into the liquid chamber from its proximal end and is configured to move forward and backward inside the liquid chamber;

a moving mechanism attached to the plunger to move the plunger;

a drive circuit and a control system to control the operation of the moving mechanism and that of the piezoceramic transducer, and configured to move the plunger to force the liquid through the orifice of the piezoceramic transducer in order to form and continuously sustain a substantially hemispherical sessile droplet with a diameter in the range of 300 to 500 microns and a volume of less than 100 nanoliter on the top surface of the piezoceramic transducer, a power supply to provide power to the moving mechanism and the piezoceramic transducer, and wherein, a Mega Hertz vibration of the sessile droplet of less than 100 nanoliter generates an aerosol with droplet sizes of only less than 5 microns from a top surface of the sessile drop.

2. The ultrasonic nebulizer of claim 1, wherein the piezoceramic transducer is a circular and coated piezoceramic.

3. The ultrasonic nebulizer of claim 1, wherein the moving mechanism comprises of a motor that rotates a screw shaft in both clockwise and counterclockwise rotational directions, and wherein the screw shaft is connected to a moving rod through a connecting rod, and wherein the moving rod is connected to the plunger, whereby the clockwise and counterclockwise rotations of the screw shaft can move the plunger forward and backward.

4. The ultrasonic nebulizer of claim 1, wherein the moving mechanism comprises of a motor that moves a central shaft backward and forward, and wherein the central shaft is connected to the plunger, whereby the movement of the central shaft can move the plunger forward and backward.

5. The ultrasonic nebulizer of claim 1, wherein the moving mechanism is a linear motion motor.

6. The ultrasonic nebulizer of claim 1, wherein the diameter of the orifice is less than 500 microns.

7. The ultrasonic nebulizer of claim 1, wherein the nebulizer is substantially cylindrical comprising of a cylindrical liquid chamber.

8. The ultrasonic nebulizer of claim 1, further having a housing to house a set of nebulizer components and having an attachable mouth piece that has an aerosol port.

9. The ultrasonic nebulizer of claim 1, wherein the nebulizer has air inlets and air channels to allow an inlet air to enter the nebulizer and pass through the air channels to reach the mouth piece and mix with the aerosol generated by the piezoceramic transducer.

10. The ultrasonic nebulizer of claim 9, further having air filters to filter the inlet air.

11. The ultrasonic nebulizer of claim 1, further having an air swirler to swirl the air before entering the mouth piece.

12. The ultrasonic nebulizer of claim 1, further having an ON/OFF switch to control a duration of the ON time.

13. The ultrasonic nebulizer of claim 1, wherein the power supply is a rechargeable battery.

14. The ultrasonic nebulizer of claim 1, wherein the control system is configured to provide a variable frequency and variable power signal to the piezoceramic transducer.

15. A meshless ultrasonic nebulizer comprising:

a casing having a first section and a second section, wherein the first section has a set of air inlets to allow air to enter into the casing, and the second section is an elongated section that has an opening configured to receive a mouth piece and allows air to exit the casing;

a liquid chamber placed inside the elongated section of the second section of the casing and having a proximal end, a distal end, and a volume to receive a liquid having a set of properties, and wherein the distal end is aligned towards the opening of the casing;

a piezoceramic transducer consisting of an orifice at its center and attached to the distal end of the liquid chamber, wherein the piezoelectric is operable in a range of 1-5 Mega Hertz frequency, wherein a back side of the piezoceramic transducer faces the liquid and a front planar side of the piezoceramictransducer faces the opening of the casing;

a plunger movably and sealably inserted into the liquid chamber from its proximal end and is configured to move forward and backward inside the liquid chamber;

a motor placed in the first section of the casing that rotates a screw shaft in both clockwise and counterclockwise rotational directions;

a connecting rod connecting the screw shaft to the plunger, whereby the clockwise and counterclockwise rotations of the screw shaft moves the plunger forward and backward;

a drive circuit and a control system to control the operation of the motor and the piezoceramic transducer, and configured to move the plunger to force the liquid through the orifice of the piezoceramic transducer in order to form and continuously sustain a substantially hemispherical sessile droplet with a diameter in the range of 300 to 500 microns and a volume of less than 100 nanoliter on the top surface of the piezoceramic transducer, wherein a Mega Hertz vibration of the sessile droplet of less than 100 nanoliter generates an aerosol with droplet sizes of only less than 5 microns from a top surface of the sessile drop;

a battery placed inside the casing and connected to an ON/OFF switch placed on a side of the casing to provide powerto the motor and the piezoceramic transducer and to control a duration of the ON time, and an air swirler set around the liquid chamber and in the elongated section of the casing to swirl the air that enters the casing through the set of air inlets before entering the mouth piece, thereby keeping the aerosol at the center of the mouth piece, preventing any wall collisions.

* * * * *